US012702670B2

(12) United States Patent
Hamilton et al.

(10) Patent No.: US 12,702,670 B2
(45) Date of Patent: Aug. 11, 2026

(54) COMPOSITIONS AND METHODS FOR TREATING BREAST CANCER

(71) Applicant: The Regents of the University of California, Oakland, CA (US)

(72) Inventors: Nalo M. Hamilton, Los Angeles, CA (US); Diana C. Marquez-Garban, Culver City, CA (US); Richard J. Pietras, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 747 days.

(21) Appl. No.: 17/926,408

(22) PCT Filed: May 21, 2021

(86) PCT No.: PCT/US2021/033547

§ 371 (c)(1),
(2) Date: Nov. 18, 2022

(87) PCT Pub. No.: WO2021/237022

PCT Pub. Date: Nov. 25, 2021

(65) Prior Publication Data

US 2023/0181593 A1 Jun. 15, 2023

Related U.S. Application Data

(60) Provisional application No. 63/028,337, filed on May 21, 2020.

(51) Int. Cl.

| | |
|---|---|
| ***A61K 31/53*** | (2006.01) |
| ***A61K 31/4166*** | (2006.01) |
| ***A61K 31/519*** | (2006.01) |
| ***A61K 39/395*** | (2006.01) |
| ***A61P 35/00*** | (2006.01) |

(52) U.S. Cl.
CPC .......... *A61K 31/53* (2013.01); *A61K 31/4166* (2013.01); *A61K 31/519* (2013.01); *A61K 39/39558* (2013.01); *A61P 35/00* (2018.01)

(58) Field of Classification Search
CPC .. A61K 31/53; A61K 31/4166; A61K 31/519; A61K 39/39558; A61P 35/00
See application file for complete search history.

(56) References Cited

FOREIGN PATENT DOCUMENTS

| | | | |
|---|---|---|---|
| WO | WO-2016/040880 | A1 | 3/2016 |
| WO | WO-2019/094832 | A1 | 5/2019 |
| WO | WO-2020/092743 | A2 | 5/2020 |
| WO | WO-2021/237022 | A1 | 11/2021 |

OTHER PUBLICATIONS

PubChem [Internet]. Bethesda (MD): National Library of Medicine (US), National Center for Biotechnology Information; 2004—. PubChem Compound Summary for CID 57379345, Ceritinib; [cited Jun. 3, 2025]. Available from: https://pubchem.ncbi.nlm.nih.gov/compound/Ceritinib (Year: 2012).*
Simpson, Aaron et al. "Insulin-Like Growth Factor (IGF) Pathway Targeting in Cancer: Role of the IGF Axis and Opportunities for Future Combination Studies." Targeted oncology vol. 12,5 (2017): 571-597. doi:10.1007/s11523-017-0514-5 (Year: 2017).*
Davis M, Tripathi S, Hughley R, et al. AR negative triple negative or "quadruple negative" breast cancers in African American women have an enriched basal and immune signature. PLoS One. 2018;13(6):e0196909. Published Jun. 18, 2018. doi:10.1371/journal.pone.0196909 (Year: 2018).*
Hamilton et al., Int. J. Mol. Sci., 18(2305):1-15 (2017) (Year: 2017).*
Huang et al., Breast Cancer, 27:527-533 (2020) (Year: 2020).*
Phipps et al., Breast Cancer Res. Treat., 126:671-678 (2011) (Year: 2011).*
Davison, Neoplasia, 13(6):504-515 (2011) (Year: 2011).*
Litzenburger et al., Cancer Res., 69(24-Suppl):1132 (2009) (Year: 2009).*
Sachdev et al., Cancer Res., 75(9-Suppl):P1-07-03 (2015) (Year: 2015).*
Bano et al., "Analyzing structural differences between insulin receptor (IR) and IGF1R for designing small molecule allosteric inhibitors of IGF1R as novel anti-cancer agents." Growth Hormone & IGF Research, 55, 101343, (2020).
Carboni et al., "BMS-754807, a small molecule inhibitor of insulin-like growth factor-1R/IR," Mol Cancer Thera, 8(12): 3341-3349 (2009).
Hamilton Patent Application May 2020 Background.
International Search Report and Written Opinion for International Application No. PCT/US2021/033547 mailed Sep. 9, 2021.
Invitation to Pay Additional Fees for International Application No. PCT/US2021/033547 mailed Aug. 23, 2021.
Nalo et al., "Combination of insulin-like growth factor-1 receptor/insulin receptor (IGF1R/IR) antagonist with anti-PD-L1 antibody blocks triple-negative breast cancer (TNBC) progression," Cancer Res, 80(16) (2020).
NCT: 0239625, "Study of Safety and Efficacy of Ceritinib in Combination With Nivolumab in Patients With ALK-positive Non-small Cell Lung Cancer," (8 pages) (2015).
Traina et al., "Enzalutamide for the treatment of androgen receptor-expressing triple-negative breast cancer," J Clin Oncol, 36(9): 884-892(2008).
UCLA Technology Development Froup IR Form May 8, 2020.
Melnick et al., "Abstract A040: BMS-754807 inhibits the survival of triple-negative breast cancer tumors by regulating cargo in small extracellular vesicles (sEV)", Proceedings of the 18th AACR Conference on the Science of Cancer Health Disparities; Sep. 18-21, 2025; Baltimore, MD. Philadelphia (PA): AACR; Cancer Epidemiol Biomarkers Prev 2025;34(9 Suppl):Abstract nr A040.

* cited by examiner

*Primary Examiner* — Thomas J. Visone
(74) *Attorney, Agent, or Firm* — Foley Hoag LLP; David P. Halstead; Alexander J. Chatterley

(57) ABSTRACT

The present disclosure relates to methods and compositions for the treatment of cancer (e.g., breast cancer).

19 Claims, 12 Drawing Sheets

FIG. 1

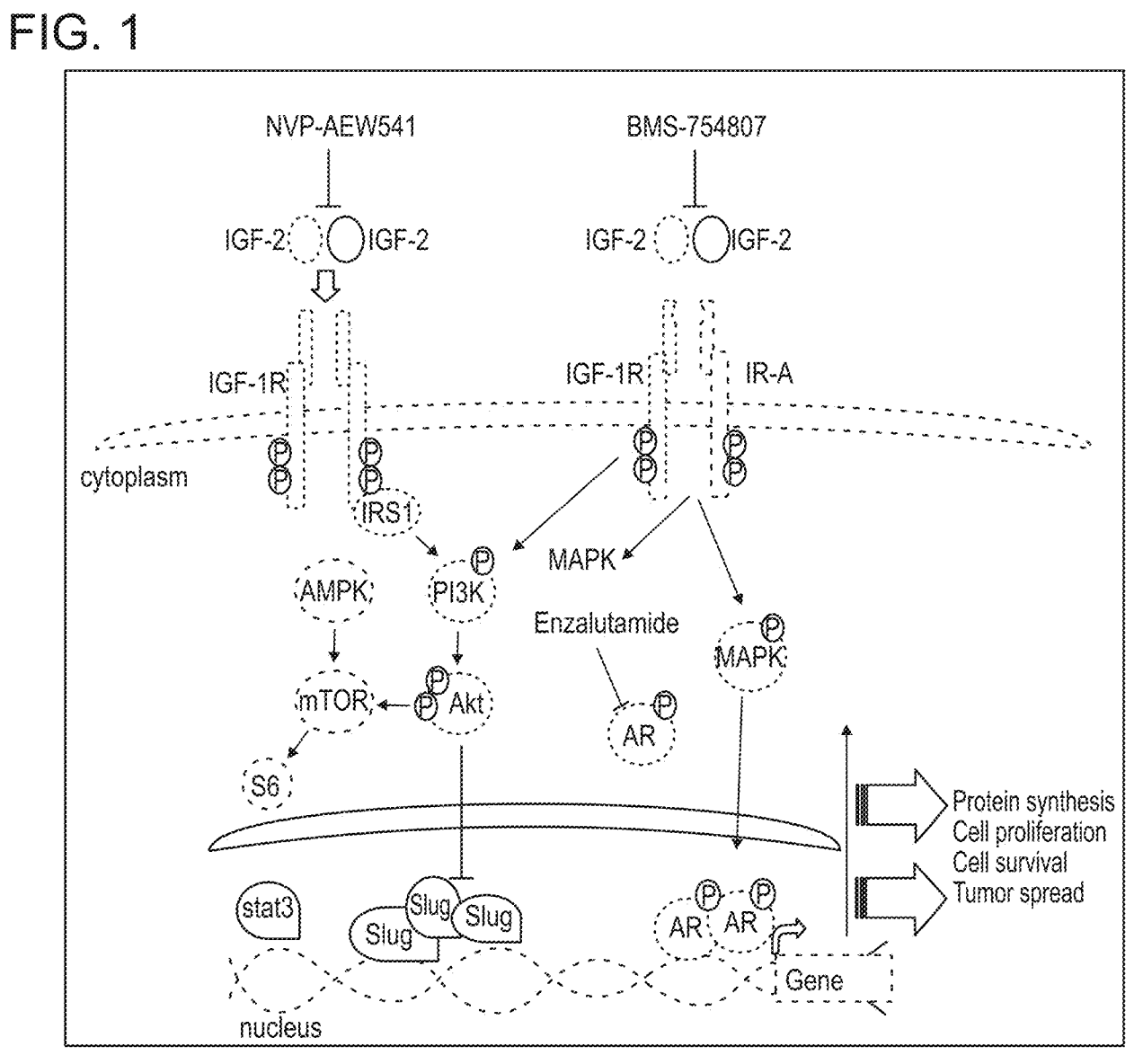

NVP-AEW541
BMS-754807
IGF-2
IGF-2
IGF-2
IGF-2
IGF-1R
IGF-1R
IR-A
P
IRS1
PI3K
MAPK
MAPK
Enzalutamide
AR
AMPK
mTOR
Akt
S6
Protein synthesis
Cell proliferation
Cell survival
Tumor spread
Slug
Slug
Slug
Slug
AR
AR
Gene
stat3
nucleus
cytoplasm MDA-MB-231
Vehicle
BMS/NVP
IGF2 100 ng/ml
Relative Wound Density (Percent)
0
10
20
30
40
50
60
70
80
90
100
Time (Hours)
0
10
15
20
25
30
35
40
45
50

% of CD11b+ cells
60
50
40
30
20
10
0
*
*
*
*
Total MDSC
PMN-MDSC
CON
Ab
BMS
BMS+Ab % CD8+ cells
25
20
15
10
5
0
*
*
*
CON
Ab
BMS
BMS+Ab
% CD4+ cells
2
1.6
1.2
0.8
0.4
0
*
**
CON
Ab
BMS
BMS+Ab

COMPOSITIONS AND METHODS FOR TREATING BREAST CANCER

RELATED APPLICATIONS

This application is the § 371 National Stage of PCT/US2021/033547, filed May 21, 2021, which claims the benefit of U.S. Provisional Application No. 63/028,337 filed May 21, 2020, the contents of each of which are fully incorporated by reference herein.

GOVERNMENT SUPPORT

This invention was made with government support under Grant No. CA143930, awarded by the National Institutes of Health. The government has certain rights in the invention.

BACKGROUND

Triple-negative breast cancer (TNBC) is a BC subtype that accounts for about 15% of all BC cases at diagnosis, yet almost half of all BC deaths are attributed to TNBC. TNBCs lack estrogen receptor-α (ERα), progesterone receptor (PR) and human epidermal growth factor receptor-2 (HER2) overexpression. Consequently, TNBC cannot be treated with current targeted therapeutics for ER-positive or HER2 over-expressing tumors. TNBC is heterogeneous and tends to occur often among premenopausal and African American women. In the clinic, TNBC has been found to be associated with a range of adverse biological features including high mitotic count and aggressive behavior with a highly metastatic phenotype and early relapse. Due to a poor understanding of the biology of TNBC progression coupled with the lack of approved targeted therapies for patients with this aggressive disease, TNBC continues to ravage a population of women in the prime of their lives. Accordingly, there is an ongoing need for new treatments of certain breast cancers, such as triple negative breast cancer.

SUMMARY OF THE INVENTION

TNBC patient mortality is disproportionately high compared to all other breast cancer subtypes. Although immune checkpoint inhibitors alone or combined with chemotherapies are reported to have antitumor efficacy in about 20-30% of TNBC patients in the clinic, these promising targeted therapies are not available to most patients with this deadly form of breast cancer. Emerging evidence including preliminary data highlighted below (presented below) points to significant links between TNBC progression and immune cell subpopulations in the tumor microenvironment.

In one aspect, the present disclosure provides methods of treating cancer (e.g., breast cancer) in a subject in need thereof comprising conjointly administering an inhibitor of insulin-like growth factor receptor 1 (IGF1R) and an inhibitor of insulin receptor (IR) to the subject. In certain such embodiments, the methods further comprise conjointly administering an immune checkpoint inhibitor to the subject.

In another aspect, the present disclosure provides compositions comprising an inhibitor of insulin-like growth factor receptor 1 (IGF1R), an inhibitor of insulin receptor (IR), an immune checkpoint inhibitor, and an excipient.

In another aspect, the present disclosure provides compositions comprising an inhibitor of insulin-like growth factor receptor 1 (IGF1R), an inhibitor of insulin receptor (IR), and an excipient; wherein the IGF1R inhibitor and the IR inhibitor are different (e.g., the IGF1R inhibitor is BMS-754807 and IR the inhibitor NVP-AEW541).

BRIEF DESCRIPTION OF THE DRAWINGS

FIG. 1 is a schematic of the IGF1R Signaling Pathway. Hormone IGF2 is able to bind to homodimers of IGF1R or the heterodimer of IGF1R and the insulin receptor (IR) thereby initiating downstream signaling via MAPK or PI3K/AKT pathways to stimulate intracellular activity to promote tumor proliferation and metastasis. In TNBC cells inhibition of signaling pathways by NVP-AEW541, IGF1R inhibitor, and/or BMS-754807, an IGF1R/IR inhibitor, alone or in combination with enzalutamide, an AR inhibitor, reduce TNBC proliferation, survival and metastasis. Additionally, IGF1R/IR antagonist reduce the expression of AR and SLUG in vitro.

FIG. 4A shows the results in media containing vehicle. Magnification 100×. P<0.05. FIG. 4B shows the results in media containing IGF2. Magnification 100×. P<0.05. FIGS. 4C & D show conditioned media containing a combination of IGF1R/IR antagonists. Wound closure is significantly inhibited. BMS/NVP=BMS-754807 (20 uM) and NVP-AEW541 (8 uM).

FIG. 6A shows that the combination therapy with BMS+anti-PD-L1 antibody suppresses TNBC progression in vivo as compared to appropriate controls (P<0.01, *P<0.001, t-test). FIG. 6B displays high dimensional analysis of mass cytometry data from single cell suspensions purified from 4T1 tumors in A harvested at treatment day 9. Combination treatment significantly decreases myeloid derived suppressor cells, total and polymorphonuclear (PMN-MDSC) after combination therapy as compared to controls (*P<0.05). FIG. 6C shows that combination therapy with BMS and Ab increases effector CD8+ and CD4+ tumor infiltrating lymphocytes (TILs). FIG. 6D shows that the population of T central memory cells in spleens of mice is also significantly increased (*P<0.05, **P<0.01, t-test).

DETAILED DESCRIPTION OF THE INVENTION

Figure 2:
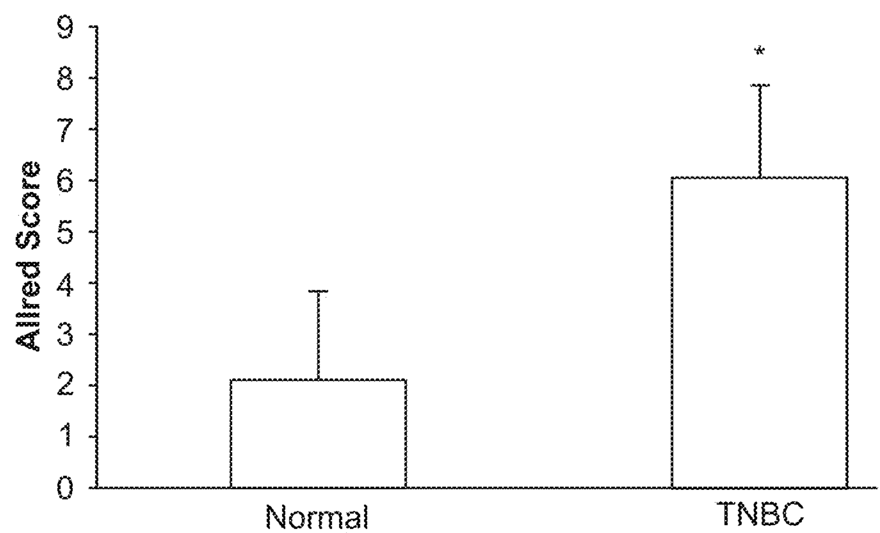
FIG. 2 depicts the results of an evaluation of IGF2 in TNBC tumors. A modified Allred Score was obtained based on the proportion of sample stained and staining intensity. Error bar represents standard deviation. * P<0.05. IGF2 was present at higher concentrations in TNBC as compared to the control.

Investigations into targeted therapies for TNBC offer evidence for the insulin-like growth factor-1 receptor (IGF1R) pathway as a promising new target. However, randomized trials have yet to show a clear clinical benefit of targeting the IGF1R pathway in combination with conventional cancer treatments. This may be due, in part, to 1) a lack of predictive biomarkers for drug targeting, 2) incomplete understanding of receptor functions and cross-communication with other downstream pathways and 3) an absence of rational combination therapy regimens. The TNBC subtype is considered 'unstable' as recurrent or metastatic biomarkers may vary from the primary tumor. Such changes may be due, in part, to insulin-like growth factor (IGF) signaling that regulates breast cancer (BC) proliferation, invasion and survival. Several reports show increased insulin-like growth factor 2 (IGF2) expression in archival TNBC specimens, notably those of AA and Latina women and TNBC progression associates with high levels of IGF28. TNBCs also have high stromal/epithelial expression of IGF2, indicating that IGF2 paracrine/autocrine pathways may modulate the TME. When bound by IGF2, tyrosine kinase receptors including insulin receptor isoform A (IR-A) and insulin-like growth factor-1 receptor (IGF1R) activate downstream mitogen-activated protein kinase (MAPK) and PI3K-AKT/protein kinase B pathways. In the absence of androgens and estrogens, IGF2 binding to IGF1R and IR-A modulates activation of downstream effectors including androgen receptors (AR) and Slug, a meditator of metastasis effects blocked by IGF1R/IR inhibitors (FIG. 1). This relationship may be important because AR expression is known from independent clinical studies to associate with aggressive, metastatic BCs and is notably enriched in specific subtypes of TNBC15. Not only is AR highly conserved and associated with TNBC progression, but significant crosstalk between AR and IGF1R/IR, have been previously documented.

Cancer immunotherapy such as use of immune checkpoint inhibitors (ICI) is emerging as a cornerstone of treatment; however, response rates in TNBC are generally less than 20-30%. Tumor-infiltrating lymphocytes (TILs) at the tumor site are an important prognostic factor in TNBC, and memory CD8+ T-cells are a key component of protective immunity. Studies demonstrate that TNBC have a higher rate of CD8+ T-cell infiltration suggesting that treatment for TNBC should include immunotherapy. PD-L1, a ligand for programmed cell death protein-1 (PD-1), is overexpressed on TNBC tumors. Elevated PD-L1 expression is associated with higher tumor grade, the absence of estrogen and progesterone receptors as well as larger tumor size. Used by tumor cells to evade the immune response mounted by tumor specific T-cells, studies indicate that upregulation of PD-L1 is due in part to PTEN down regulation and increased PI3K/Akt signaling. Current clinical trials are investigating the promise of combination therapies consisting of ICIs with other agents to treat TNBC.

Myeloid-derived suppressor cells (MDSCs) are reported to promote tumor growth, development and metastasis. One pathway used by MDSCs to exert these effects involves the PTEN/Akt pathway. Via this pathway MDSCs downregulate PTEN while upregulating Akt signaling and the expression of proteins that promote tumor cell invasion and metastasis. Emerging studies reveal that elevated MDSCs in malignancy contribute to ICI resistance and suggest that targeting MDSCs may be a way to improve the antitumor efficacy of immunotherapies such as ICIs.

Although preclinical data using IGF1R inhibitors initially showed great promise in preclinical studies a lack of significant antitumor activity in previous clinical trials including breast cancer patients has been reported. This problem in clinical translation may well have been due to the lack of an identifiable biomarker, poor selection of a target patient population or monotherapy limitations. It is suggested that the co-targeting of IGF1R and IR is needed to inhibit tumor growth and reduce disruption of endocrine system. Using TNBC models in vivo, it has been found that current immunotherapies can be significantly amplified by combining ICIs with IGF1R inhibitors alone and/or potentially combined with AR and/or IR inhibitors, thereby targeting critical steps in TNBC tumor recognition and elimination by the natural immune system.

In one aspect, the present disclosure provides methods of treating cancer (e.g., breast cancer) in a subject in need thereof comprising conjointly administering an inhibitor of insulin-like growth factor receptor 1 (IGF1R) and an inhibitor of insulin receptor (IR) to the subject. In certain embodiments, the method further comprises conjointly administering an immune checkpoint inhibitor to the subject. In certain embodiments, the method further comprises conjointly administering an androgen receptor antagonist to the subject.

In another aspect, the present disclosure provides methods of treating cancer (e.g., breast cancer) in a subject in need thereof comprising conjointly administering an inhibitor of insulin-like growth factor receptor 1 (IGF1R) and an immune checkpoint inhibitor to the subject.

In another aspect, the present disclosure provides methods of treating cancer (e.g., breast cancer) in a subject in need thereof comprising conjointly administering an inhibitor of insulin receptor (IR) and an immune checkpoint inhibitor to the subject.

In certain embodiments, IGF1R inhibitor is selected from dalotuzumab, MK-2206, ridaforolimus, MK-0752, NVP-AEW541, cetuximab, irinotecan, cisplatin, etoposide, ridaforolimus, figitumumab, carboplatin, paclitaxel, dexamethasone, docetaxel, prednisone, everolimus, ganitumab, exemestane, fulvestrant, folfiri, gemcitabine, panitumumab, sorafenib, linsitinib, R1507, and BMS-754807 or a pharmaceutically acceptable salt thereof; or a combination of any of the foregoing. In certain embodiments, the IGF1R inhibitor is selected from dalotuzumab, MK-2206, ridaforolimus, MK-0752, NVP-AEW541, cetuximab, irinotecan, etoposide, ridaforolimus, figitumumab, everolimus, ganitumab, exemestane, fulvestrant, folfiri, panitumumab, sorafenib, linsitinib, R1507, and BMS-754807 or a pharmaceutically acceptable salt thereof; or a combination of any of the foregoing. In certain preferred embodiments, the IGF1R inhibitor is BMS-754807.

In certain embodiments, the IR inhibitor is selected from linsitinib, ceritinib, BMS-754807, 5961 TFA, 5961, BMS-536924, NVP-AEW541, AGL-2263, GSK1838705A, NVP-TAE 226, AG1024, MSDC 0160, NVP-ADW742, kaempferitrin, rhoifolin, and KU14R or a pharmaceutically acceptable salt thereof. In certain preferred embodiments, the IR inhibitor is BMS-754807.

In certain embodiments, the IGF1R inhibitor and IR inhibitor are the same (e.g., the IGF1R inhibitor is BMS-754807 and IR the inhibitor BMS-754807). In other embodiments, the IGF1R inhibitor and IR inhibitor are the different (e.g., the IGF1R inhibitor is BMS-754807 and IR the inhibitor NVP-AEW541).

In certain preferred embodiments, the method further comprises conjointly administering an immune checkpoint inhibitor to the subject. In certain embodiments, the immune checkpoint inhibitor is an inhibitor of CD27, CD28, CD80, CD86, CD40, CD122, CD137, OX40, GITR, ICOS, A2AR, B7-HR, BTLA, CTLA-4, IDO, KIR, LAG3, NOX2, PD-1, PD-L1, PD-L2, TIM-3, VISTA, or SIGLEC7. In certain embodiments, the immune checkpoint inhibitor is an inhibitor of PD-1, PD-L1, or PD-L2. In certain preferred embodiments, the immune checkpoint inhibitor is an inhibitor of PD-L1. In certain embodiments, the immune checkpoint inhibitor is an antibody or a small molecule. In certain embodiments, the immune checkpoint inhibitor is an antibody. In certain embodiments, the antibody is polyclonal antibody, an intact monoclonal antibody, an antibody fragments, a single chain Fv (scFv), a chimeric antibody, a humanized antibody, or a fusion proteins. In certain embodiments, the immune checkpoint inhibitor is a small molecule. In certain embodiments, the immune checkpoint inhibitor is selected from anti-CD274/B7-H1/PD-L1 clone 10F.9G2, atezolizumab, avelumab, cemiplimab, durvalumab, cemiplimab, nivolumab, pembrolizumab, KB035, CK-301, AUNP12, CA-170, and BMS-986189 or a pharmaceutically acceptable salt thereof.

In certain embodiments, the method further comprises conjointly administering an androgen receptor (AR) antagonist to the subject. In certain embodiments, the AR antagonist is selected from 17α-hydroyprogesterone, chlormadinone acetate, cyproterone acetate, megestrol acetate, osaterone acetrate, 19-norprogesterone, nomegestrol acetate, 10-nortestosterone, dienogest, oxendolone, 17α-spirolactone, drospirenone, spironolactone, medrogestone, bicalutamide, flutamide, nilutamide, apalutamide, darolutamide, enzalutamide, proxalutamide, cimetidine, and topilutamide or a pharmaceutically acceptable salt thereof. In certain preferred embodiments, the AR antagonist is enzalutamide or a pharmaceutically acceptable salt thereof.

In certain embodiments, the cancer is breast cancer. In certain preferred embodiments, the breast cancer is triple negative breast cancer. In other preferred embodiments, the breast cancer is quadruple negative breast cancer. In certain embodiments, the breast cancer is relapsed or refractory. In certain embodiments, the breast cancer is metastatic.

In certain embodiments, the subject is a woman. In certain embodiments, the subject is of African, African American, Latino, or Hispanic descent. In certain embodiments, the subject has a familial history of breast cancer. In certain embodiments, the subject has a familial history of triple negative breast cancer. In certain embodiments, the subject has a familial history of quadruple negative breast cancer.

In another aspect, the present disclosure provides compositions comprising an inhibitor of insulin-like growth factor receptor 1 (IGF1R), an inhibitor of insulin receptor (IR), an immune checkpoint inhibitor, and an excipient. In certain embodiments, the IGF1R inhibitor and IR inhibitor are the same (e.g., the IGF1R inhibitor is BMS-754807 and IR the inhibitor BMS-754807). In other embodiments, the IGF1R inhibitor and IR inhibitor are the different (e.g., the IGF1R inhibitor is BMS-754807 and IR the inhibitor NVP-AEW541).

In another aspect, the present disclosure provides compositions comprising an inhibitor of insulin-like growth factor receptor 1 (IGF1R), an inhibitor of insulin receptor (IR), and an excipient; wherein the IGF1R inhibitor and the IR inhibitor are different (e.g., the IGF1R inhibitor is BMS-754807 and IR the inhibitor NVP-AEW541). In certain embodiments, the composition further comprises an immune checkpoint inhibitor. In certain embodiments, the composition further comprises an androgen receptor antagonist.

In another aspect, the present disclosure provides compositions comprising an inhibitor of insulin-like growth factor receptor 1 (IGF1R) and an immune checkpoint inhibitor, and an excipient.

In another aspect, the present disclosure provides compositions comprising an inhibitor of insulin receptor (IR), an immune checkpoint inhibitor, and an excipient.

In certain embodiments, IGF1R inhibitor is selected from dalotuzumab, MK-2206, ridaforolimus, MK-0752, NVP-AEW541, cetuximab, irinotecan, cisplatin, etoposide, ridaforolimus, figitumumab, carboplatin, paclitaxel, dexamethasone, docetaxel, prednisone, everolimus, ganitumab, exemestane, fulvestrant, folfiri, gemcitabine, panitumumab, sorafenib, linsitinib, R1507, and BMS-754807 or a pharmaceutically acceptable salt thereof; or a combination of any of the foregoing. In certain embodiments, the IGF1R inhibitor is selected from dalotuzumab, MK-2206, ridaforolimus, MK-0752, NVP-AEW541, cetuximab, irinotecan, etoposide, ridaforolimus, figitumumab, everolimus, ganitumab, exemestane, fulvestrant, folfiri, panitumumab, sorafenib, linsitinib, R1507, and BMS-754807 or a pharmaceutically acceptable salt thereof; or a combination of any of the foregoing. In certain preferred embodiments, the IGF1R inhibitor is BMS-754807.

In certain embodiments, the IR inhibitor is selected from linsitinib, ceritinib, BMS-754807, 5961 TFA, 5961, BMS-536924, NVP-AEW541, AGL-2263, GSK1838705A, NVP-TAE 226, AG1024, MSDC 0160, NVP-ADW742, kaempferitrin, rhoifolin, and KU14R or a pharmaceutically acceptable salt thereof. In certain preferred embodiments, the IR inhibitor is BMS-754807.

In certain preferred embodiments, the composition further comprises an immune checkpoint inhibitor to the subject. In certain embodiments, the immune checkpoint inhibitor is an inhibitor of CD27, CD28, CD80, CD86, CD40, CD122, CD137, OX40, GITR, ICOS, A2AR, B7-HR, BTLA, CTLA-4, IDO, KIR, LAG3, NOX2, PD-1, PD-L1, PD-L2, TIM-3, VISTA, or SIGLEC7. In certain embodiments, the immune checkpoint inhibitor is an inhibitor of PD-1, PD-L1, or PD-L2. In certain preferred embodiments, the immune checkpoint inhibitor is an inhibitor of PD-L1. In certain embodiments, the immune checkpoint inhibitor is an antibody or a small molecule. In certain embodiments, the immune checkpoint inhibitor is an antibody. In certain embodiments, the antibody is polyclonal antibody, an intact monoclonal antibody, an antibody fragments, a single chain Fv (scFv), a chimeric antibody, a humanized antibody, or a fusion proteins. In certain embodiments, the immune checkpoint inhibitor is a small molecule. In certain embodiments, the immune checkpoint inhibitor is selected from anti-CD274/B7-H1/PD-L1 clone 10F.9G2, atezolizumab, avelumab, cemiplimab, durvalumab, cemiplimab, nivolumab, pembrolizumab, KB035, CK-301, AUNP12, CA-170, and BMS-986189 or a pharmaceutically acceptable salt thereof.

In certain embodiments, the composition further comprises an androgen receptor (AR) antagonist to the subject. In certain embodiments, the AR antagonist is selected from 17α-hydroyprogesterone, chlormadinone acetate, cyproterone acetate, megestrol acetate, osaterone acetrate, 19-norprogesterone, nomegestrol acetate, 10-nortestosterone, dienogest, oxendolone, 17α-spirolactone, drospirenone, spironolactone, medrogestone, bicalutamide, flutamide, nilutamide, apalutamide, darolutamide, enzalutamide, proxalutamide, cimetidine, and topilutamide or a pharmaceutically acceptable salt thereof.

In certain preferred embodiments, the AR antagonist is enzalutamide or a pharmaceutically acceptable salt thereof.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1: Treatment of TNBC

IGF2 is Highly Expressed in TNBC Tumors.

Figure 3A:
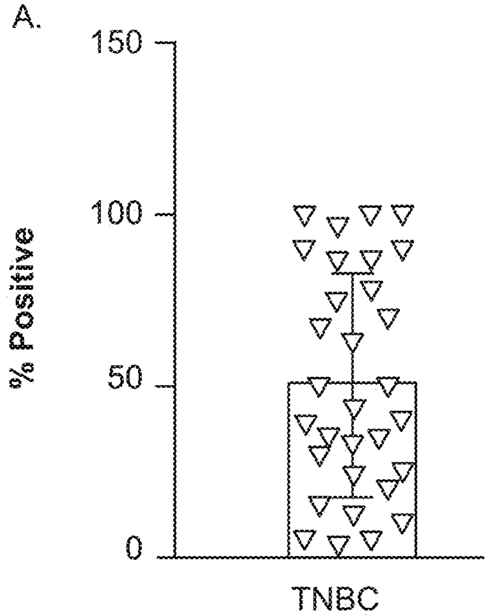
FIG. 3A shows that expression of IGF2 is expressed in 55% of archival TNBC breast tissue.
Figure 3B:
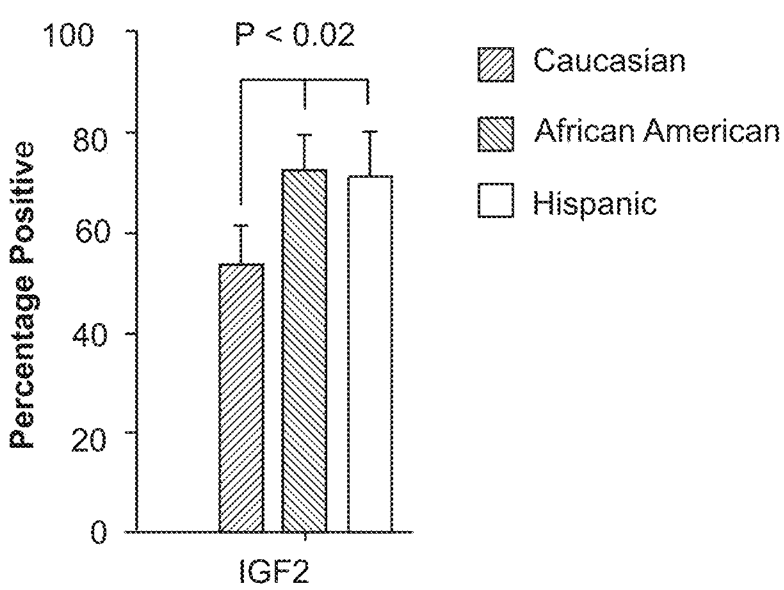
FIG. 3B shows that IGF2 positive TNBC tumors are higher in African American and Hispanic patients.

Using established Allred scoring of archival breast tissue specimens from women with TNBC (n=11) it was found that significant expression of IGF2 (P<0.01) in all TNBCs (FIG. 2), highlighting IGF2 is a potential biomarker for TNBC progression. Additionally, IGF2 was found to be highly expressed in patient derived TNBCs (FIG. 3).

Stimulation of TNBC Cell Migration by IGF2 is Inhibited by BMS-754-807 and NVP-AEW541

Figure 4A:
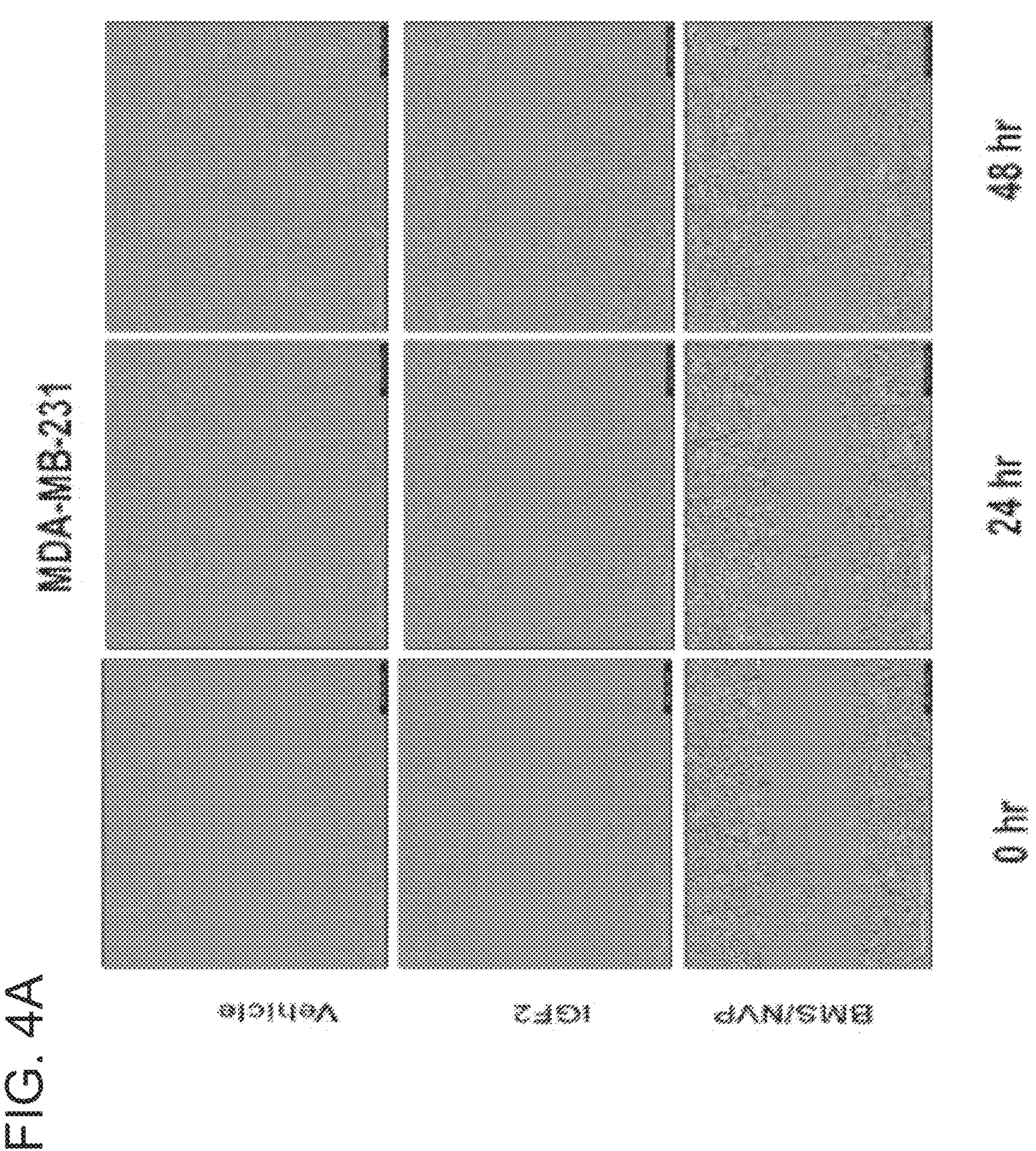
FIGS. 4A-D show that IGF1R and IR inhibitors halt TNBC migration. MDA-MB-231 and HCC 1937 TNBC cell lines were cultured in complete media in 96-welled plates. In each well 60,000 cells were plated. Scratch wounds were made using Unique WoundMaker™. Wound images were collected every 2 h for 48 h using the IncuCyte S3 Live-Cell Analysis System. Media containing IGF2 (100 ng/ml) was refreshed daily.
Figure 4B:
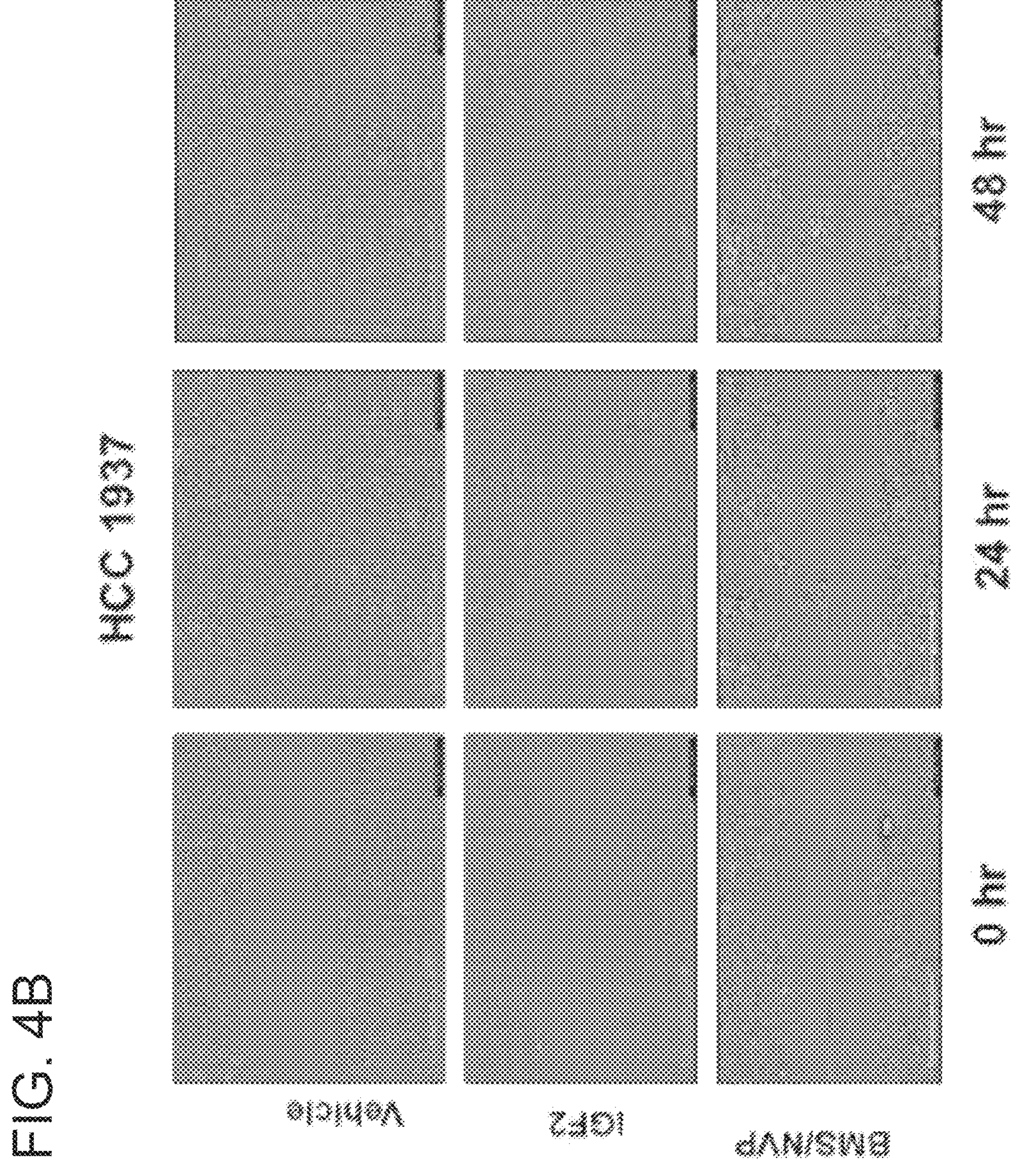
Figure 4C:
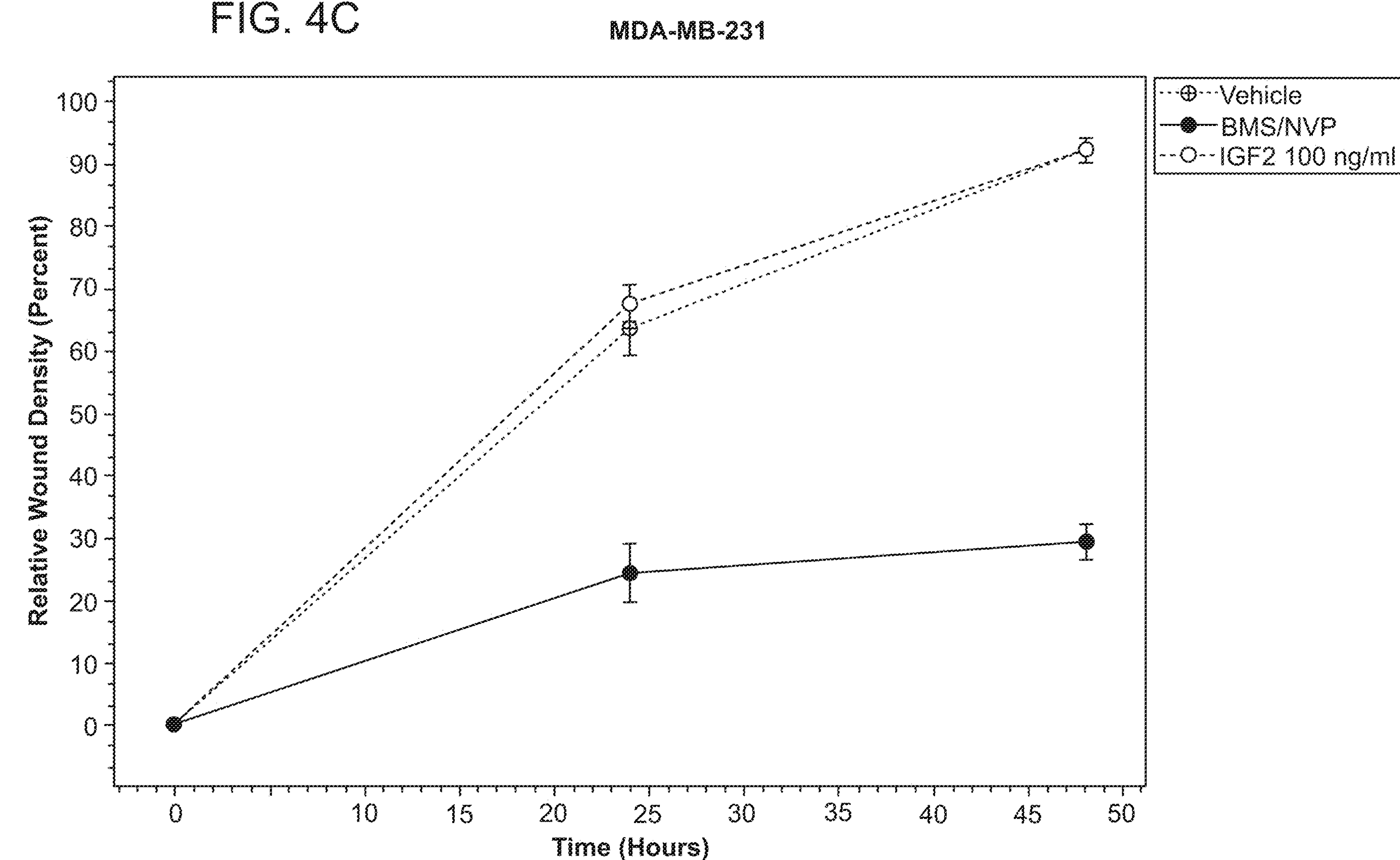
Figure 4D:
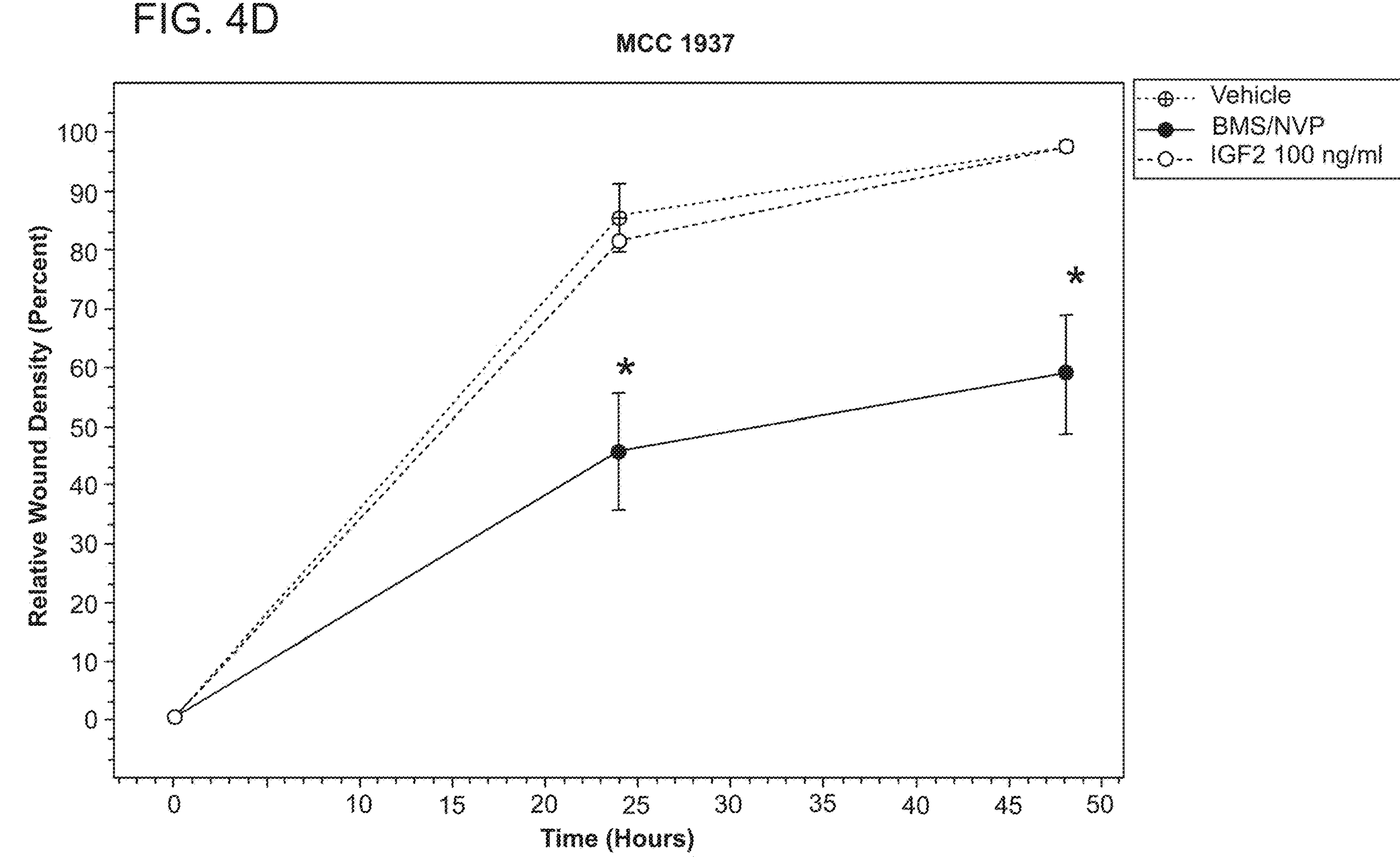

BMS-754807 (IGF1R/IR inhibitor) and NVP-AEW541 (IGF1R inhibitor) alone and combined, exhibit anti-proliferative effects on IGF2-expressing TNBC cells, an action dependent in part on AKT activity. These two inhibitors independently decrease levels of ARs in TNBC cells, indicating potential cross-talk between IGF1R/IR and AR signaling pathways. Notably, when combined with the AR inhibitor enzalutamide, these IGFR/IR inhibitors elicited a significant reduction in TNBC cell viability. In vitro TNBC cell migration is stimulated in media conditioned with IGF2 alone (FIGS. 4A & 4B). By 48 hrs both TNBC MDA-MB-231 cells and HCC 1937 cells migrated closing the wound present at 0 hours; however, this migratory process is significantly inhibited with media containing BMS-754807, dual IGF1R/IR inhibitor, +NVP-AWE541, IGF1R inhibitor, (FIGS. 4C & 4D).

IGF1R/IR and AR Combinations Reduce TNBC Viability and Tumor Progression.

Figure 5A:
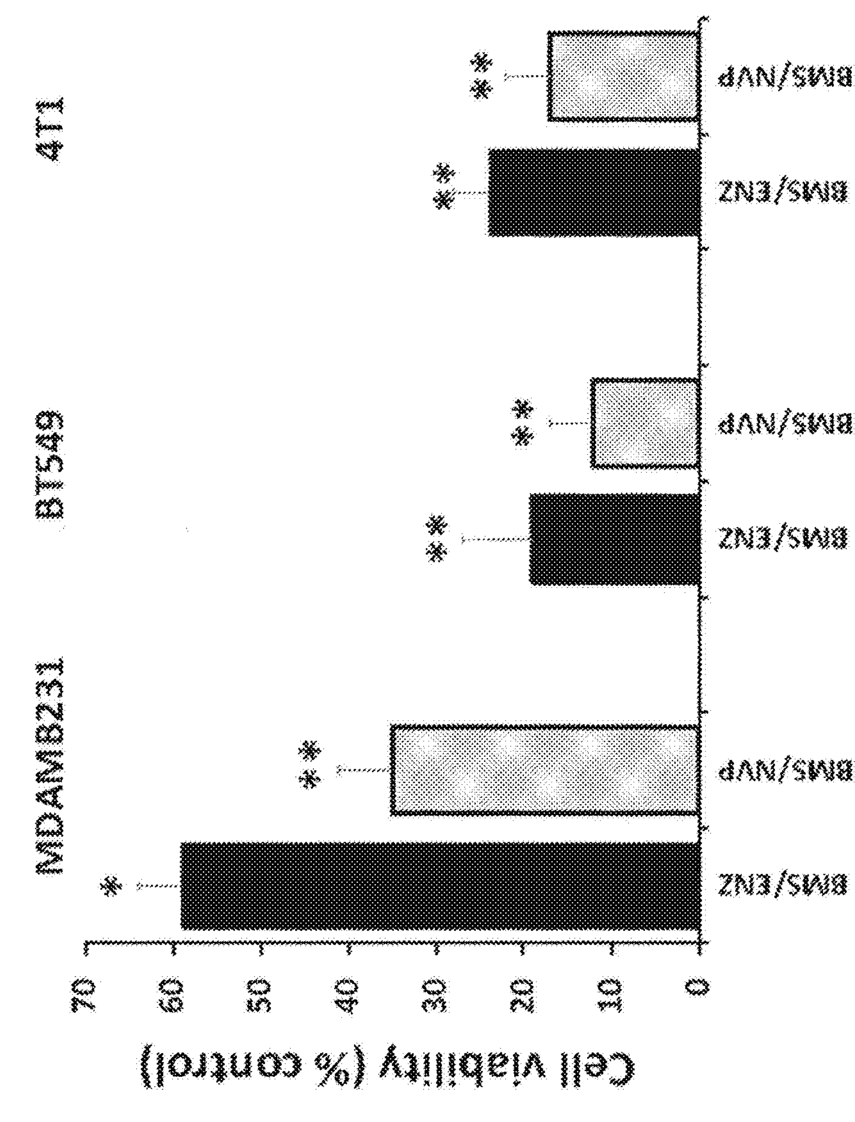
FIG. 5A shows that IGF1R/IR and enzalutamide combinations reduce human and murine TNBC growth in vitro and in vivo. After seeding TNBC cells for 24 hr, cells were exposed to selected combinations of BMS-754807 (20 μM), enzalutamide (20 μM), and NVP-AEW541 (8 μM) for 72 h. Cell viability was tested by CellTiter 96® aqueous non-radioactive cell proliferation assay (error bar=SEM; n=8; **P<0.001 *P<0.05). Results shown as % of vehicle treated controls.
Figure 5B:
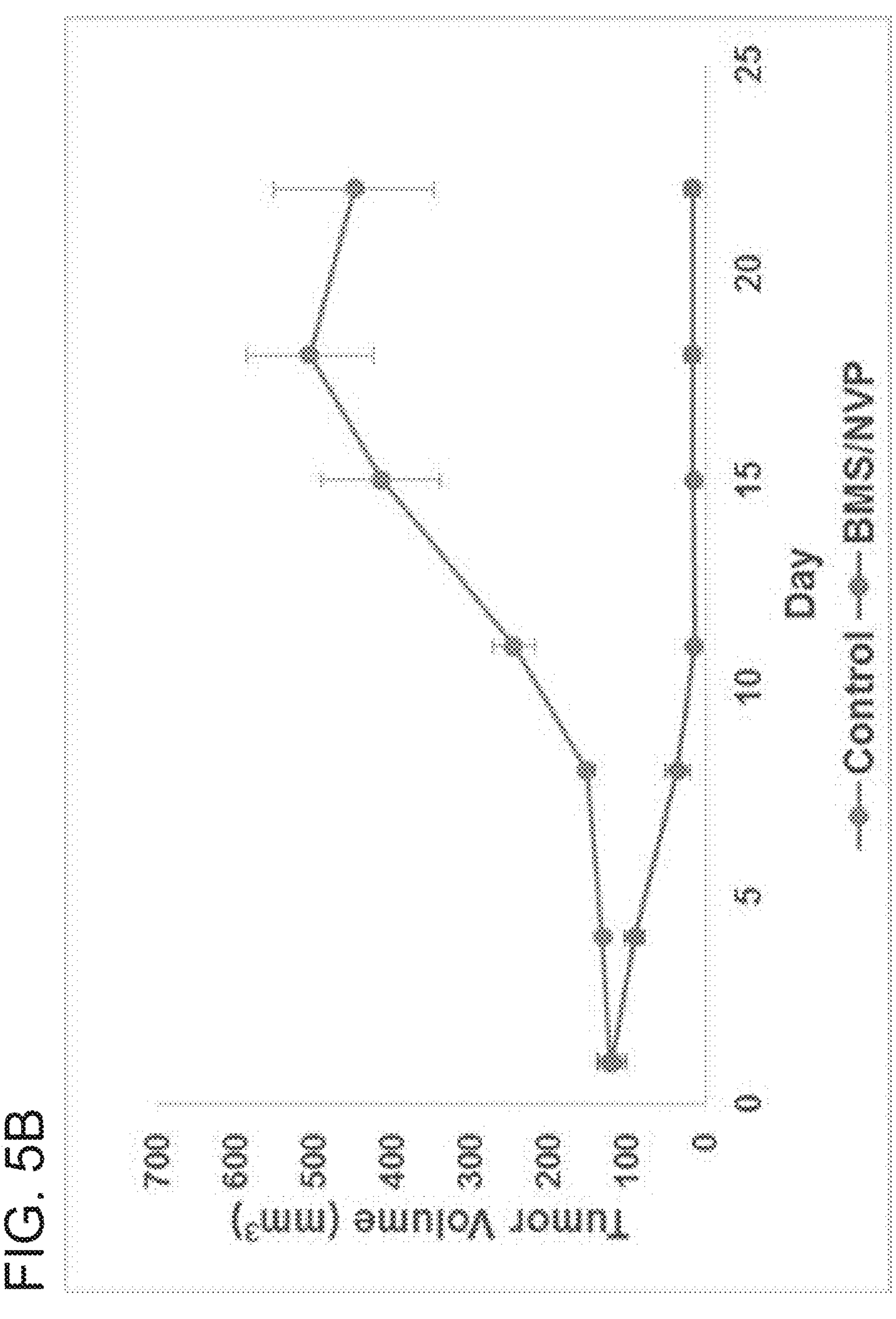
FIG. 5B shows that dual dosing of BMS-754807+NVP-AEW541 elicits significant inhibition of human TNBC tumor xenograft progression. Female nude mice (6-wk-old) were inoculated with MDA-MB-231 cells s.c. After tumors were 150 $mm_3$, mice were randomized to BMS/754807+NVPAEW541 (50 mg/kg and 20 mg/kg) or control (CON) given Qd by oral gavage. BMS/NVP has significant anti-TNBC effects (P<0.02; n=5).
Figure 6A:
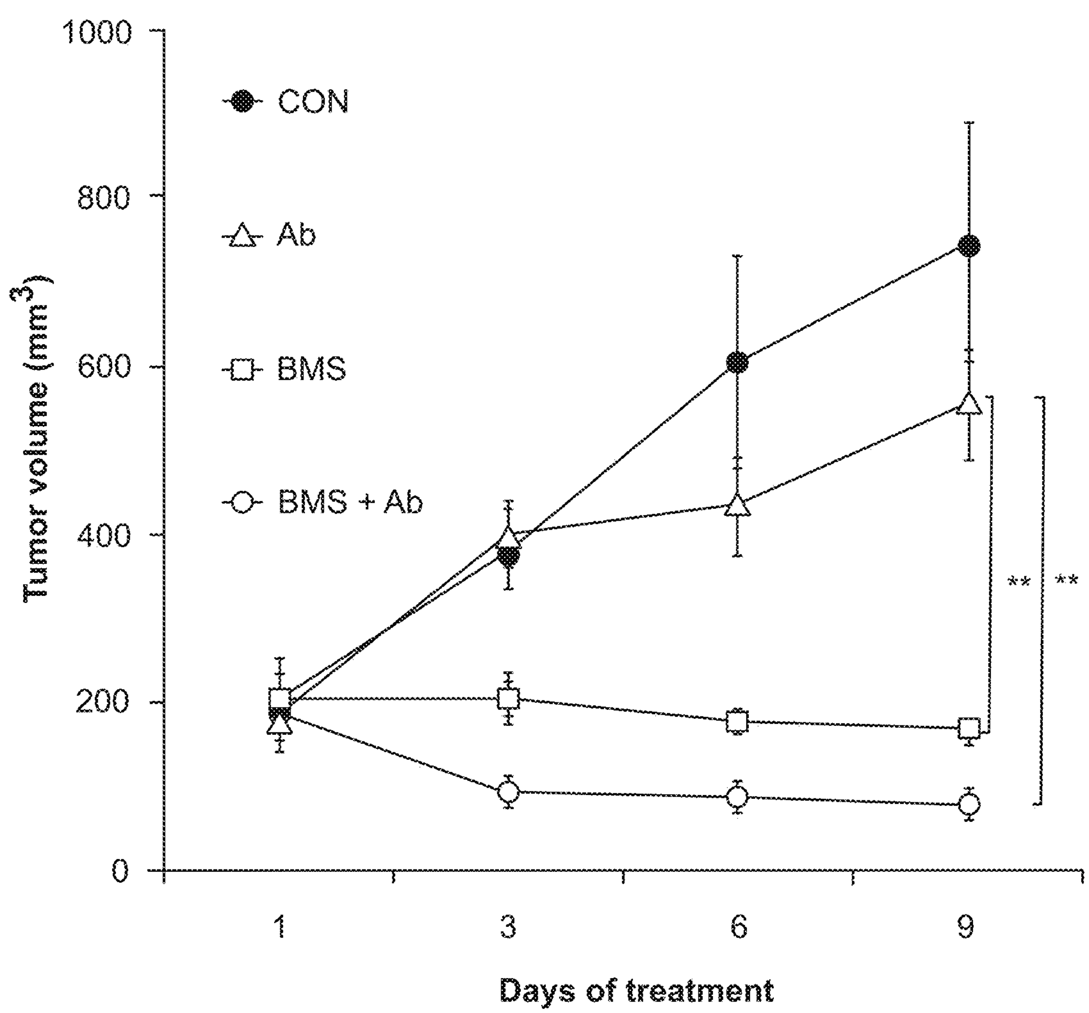
FIG. 6A-D show a combination treatment of BMS with anti PD-L1 checkpoint antibody suppresses 4T1 TNBC xenograft progression in vivo. TNBC 4T1 cells (2×105) were implanted in the mammary fat pads of BALB/c female mice (6-week old) using established methods. Mice were then randomized for treatment when tumor volumes were approx. 200 $mm_3$. Mice were treated with either vehicle control (Con), BMS 10 mg/kg, by oral gavage, daily (BMS), anti-PD-L1 checkpoint antibody from Biolegend (anti- CD274/B7-H1/PD-L1 clone 10F.9G2, 100 μg/mouse IP in PBS, Q3 days) (Ab) or combination therapy with BMS and anti-PD-L1 antibody (BMS+Ab). Tumor sizes were recorded Q 2-3 days; and mice were weighed twice weekly. Studies used 5 mice/group.
Figures 6B, 6C:
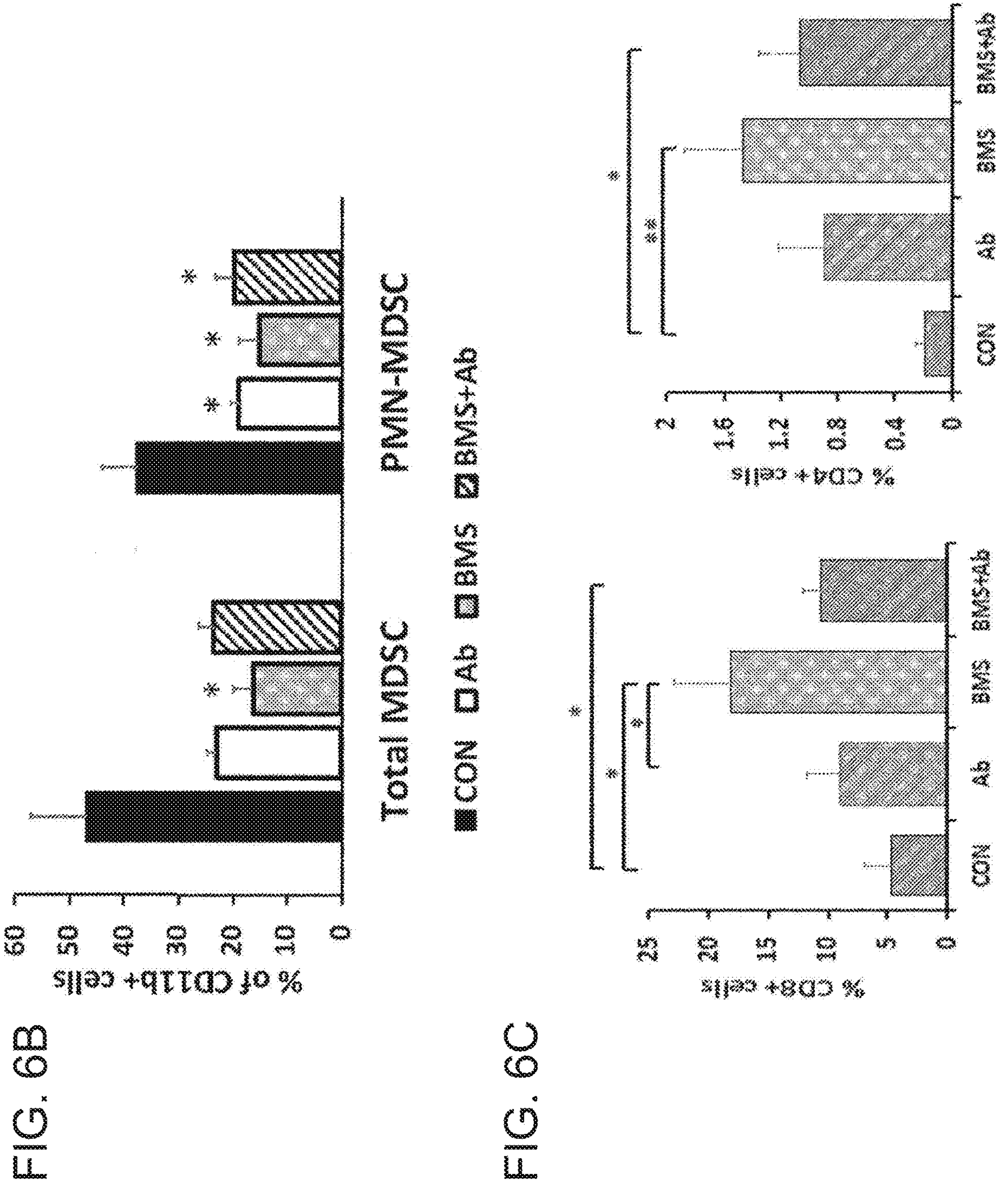
Figure 6D:
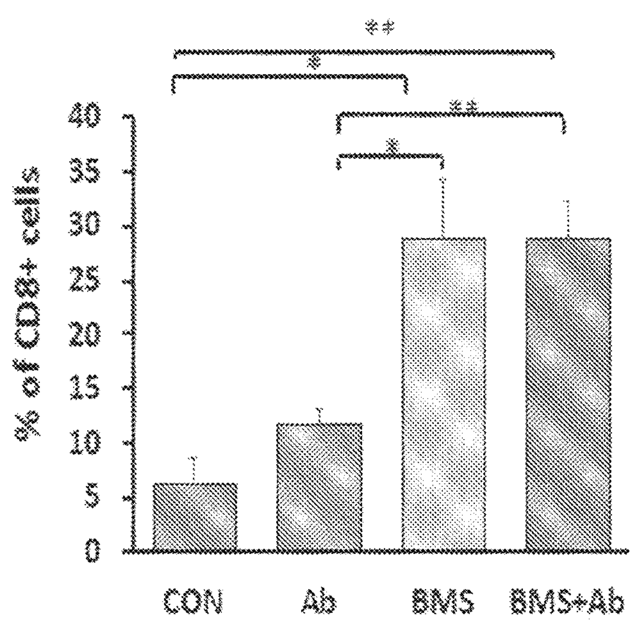
Figure 6D:
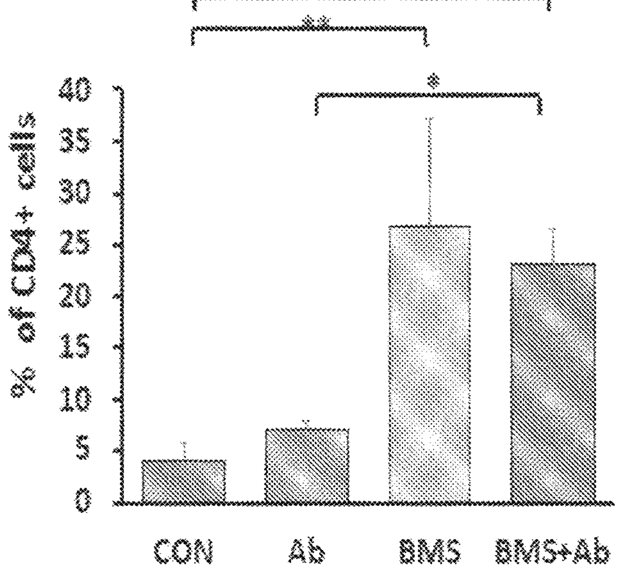

Patients with TNBC are highly likely to relapse due to tumor cell growth and metastasis. In addition to inhibiting TNBC migration, IGF1R/IR antagonists in combination with enzalutamide reduce TNBC viability (FIG. 5). The inhibition of cell viability is observed in human and murine TNBC cell cultures. The reduction of cell viability due to the combination treatments range from 40-80%. Consistently, BMS-754807+NVP-AEW541 significantly inhibited TNBC viability in each cell line assessed (P<0.001, FIG. 5A). Notably, in preclinical models, the effect of IGF1R/IR inhibitors on human TNBC xenografts in vivo was evaluated (FIG. 5B), and dual therapy with BMS-754807+NVP-AEW541 elicited significant antitumor activity (FIG. 5B). Tumor volume consistently declined in mice treated with the anti-IGF1R/IR therapy. Tumor volumes remained significantly lower than that of control for the duration of the treatment interval (P<0.02, FIG. 5B). Additionally, the effect of this combination therapy using immunohistochemistry was assessed. The inhibitory effects of BMS-754807+NVP-AEW541 was further supported by reduced staining of Ki67 in tumors obtained from experimental animals (data not shown).

BMS-754907 Potentiates Antitumor Activity of Immune Checkpoint Inhibitors in Murine 4T1 TNBC Model in Syngeneic Mice with Intact Immune System.

In vitro BMS-754807 treatment was able to reduce human TNBC cell proliferation1 and in nude mice with human xenografts in vivo, combination therapies reduced tumor volume without adverse effects (e.g. no significant change in circulating lactic acid or glucose levels, and no reduction in mouse body weight as compared to controls). Reduction of cell viability was also achieved on treatment of murine 4T1 TNBC in vitro (FIG. 6). TNBC clinical trials have shown a potential benefit of anti-PD-L1 antibodies as ICIs for anti-TNBC therapy. Notably, murine 4T1 TNBC cells express PD-L1. Thus, 4T1 cells were implanted in mammary fat pads of female syngeneic BALB/c mice to assess antitumor efficacy of BMS-754807 alone and combined with anti-PD-L1 antibodies in mice with intact immune systems (FIG. 6). After 10 days of treatment, tumors were harvested and processed for mass cytometry analyses to assess changes in immune cell subsets under different treatment conditions in FIG. 6. BMS-754807 alone and in combination with the anti-PD-L1 antibody markedly reduced tumor volume (P<0.01 & P<0.001 respectively) and decreased levels of myeloid derived suppressor cells (MDSCs, P<0.05). Additionally, the percentage of CD8+ and CD4+ tumor infiltrating lymphocytes (TILs) were significantly increased in tumor samples from the BMS-754807 and BMS754807+Ab experimental treatment groups (P<0.05).

In summary, data indicate: 1) IGF2 is significantly expressed in archival breast samples of TNBC patients, in particular African American and Latina women; 2) IGF1R/IR inhibitors stop human TNBC progression in preclinical models in vivo; 3) BMS-754807, a dual IGF1R/IR antagonist, exhibits potential synergy with ICIs in vivo by modulating specific immune cell subsets (effector and TCM TILs, MDSCs) in the TME; and 4) IGF1R/IR antagonists combination with AR antagonist, enzalutamide, reduce TNBC progression in vitro. These data suggest that combination therapies consisting of IGF1R/IR+anti-PD-L1 inhibitors have therapeutic potential for treating TNBC.

Example 2: Future Studies

Further studies aim to validate antitumor activity of IGF1R antagonists in vitro using assays for cell proliferation, apoptosis and downstream signal transduction. Antitumor activity resulting from IGF1R/IR inhibitors will be assessed in vitro using established assays for cell proliferation, apoptosis and downstream signal transduction. Retrospectively-collected, de-identified human TNBC cells from patients of diverse race, ethnicity and nonmalignant breast cells will be used as models. IGF1R/IR combined with AR inhibitors in vitro will also be assessed.

General Design.

Premenopausal women are disproportionally diagnosed with TNBC10, and some TNBC tumors also lack AR, thus denoted as quadruple-negative BC (QNBC)36. Both BC subtypes, TNBC and QNBC, lack targeted therapeutic options, but are reported to depend on glucose to maintain high rates of cell growth and express key modulators of metabolism such as IGF1R. Additionally, these tumors are found to express EGFR, a receptor that is also able to form a heterodimer with IGF1R37. Selected IGF1R/IRs plus enzalutamide combinations will be used in to assess TNBC/QNBC cell apoptosis, proliferation and other functional indices for anticancer activity, with nonmalignant cells tested in parallel.

Cell Lines

TNBC MDA-MB-231, BT549 (mesenchymal-like), and MDA-MB-468 (basal-like-1) cells 'negative' will be tested for ERα, PR, HER-2 overexpression and AR+; and QNBC HCC1937 cells 'negative' for ERα, PR, HER-2 overexpression and AR. Other cells will be chosen to represent luminal AR and basal-like-2 TNBC subtypes40 (ATCC); and early-passage TNBC or QNBC primary cell lines from de-identified patients will be available. Cultures are routinely grown in DMEM or RPMI-1640 media supplemented with antibiotic-antimycotic solution/5% FBS11. As controls, we will use non-TNBC/QNBC, ER+MCF-7 cells, non-tumor human mammary epithelial cells (HMEC) and human umbilical vein endothelial cells (HUVEC; ATCC), with each maintained in media recommended by the supplier.

Cell Proliferation/Apoptosis.

Screening assays will be done using cell proliferation ELISA-BrdU colorimetric kits (Roche), with cell numbers to be validated by cell counts. Screening for effects of BMS-75807 alone or with NVP-AEW541 or enzalutamide inhibitors on apoptosis in TNBC and control cells will be by FACS detection of annexin-V binding or TUNEL apoptosis detection using kits as per manufacturer's instructions 42.

Signal Transduction Assays. Refer to Overview of Known Cell Signaling Actions of IGF2 (FIG. 1)

Assessment of BMS-754807 alone or combination with NVP-AEW541 or enzalutamide on AMPK, AKT and mTORC1 activities. Confluent TNBC and QNBC cultures will be washed ×2 with PBS and incubated with serum-free media ×3 h. BMS-754807 (10-20 uM) alone or with NVP-AEW541 (8 uM) or enzalutatmide (20 uM) will be added with cells cultured for selected times (0-24 h). To detect AMPK activation, cells will be washed in cold PBS, lysed, and processed for SDS-PAGE. Western immunoblots are used to detect phosphorylated pAMPK (Thr172), phosphorylated ERK1/2 (Thr202/Tyr204) and phosphorylated EGFR; and total AMPK, ERK1/2, and EGFR. To find if BMS-754807 alone or with NVP-AEW541 or enzalutamide limit mTORC1 signaling in TNBC/QNBC cells, we will assess relative efficacy of IGF1R/IR/AR antagonists and rapamycin (control) to block phosphorylation of downstream mTORC1 mediators, S6K and S643-45 (FIG. 1); and inhibitory effects of AMPK inhibitors (compound C) in blocking actions of dual therapies. Combination-induced STAT3 phosphorylation inhibition will also be tested. Notably, BMS-754807 and NVP-AEW541 are reported to reduce AR via AKT which may in turn improve TORC1 inhibition1.

Measurement of Respiration in TNBC/QNBC Cells to Assess Potential Modulation of Mitochondrial Complex I with IGF1R/IR Alone or Combinations with AR Inhibitors IGF2 is able to modulate breast cancer cell metabolism and invasion, and the reduction of IGF1R activity is reported to associate with increased cellular stress. Recent studies also implicate AR as regulator of mitochondrial metabolism. Using an available Seahorse XF-96 Analyzer, oxygen consumption rates (OCR) will be assessed, extracellular acidification rates and mitochondrial function to further the understanding of the potential role of IGF1R/IR antagonists on modulation of metabolism in TNBC and QNBC cells. Metformin, a diabetic medication with anti-cancer activity that is reported to inhibit mitochondrial complex 1, will be used as a control. In this AIM, mitochondrial stress tests will also be performed on the tumor cells using oligomycin, FCCP and rotenone to confirm the cells' mitochondrial respiration were functional. Further metabolic studies will depend on results of these planned experiments.

ADME and Preliminary Toxicity Assays

ADME (solubility, microsomal and hepatocyte metabolic stability, plasma protein binding, Caco-2 permeability, hERG channel inhibition) screening and cell models/techniques to accurately predict drug-induced toxicity (including liver toxicity) services of Charles River or Cyprotex will be used to assess the candidate combinations with optimal bioavailability and potent antitumor activity.

Statistical Analysis

Triplicates of experiments will be done to verify results. Data will be presented as mean+SE and analyzed with student's t-test or other appropriate nonparametric tests. ANOVA or Kruskal-Wallis tests if outcomes are non-normally distributed will be used as appropriate to compare multiple intervention groups. Analyses will be evaluated using bar/scatter graphs with mean, standard deviation and SE displayed.

Aim 2

Assess antitumor effects and immune checkpoint inhibitor interactions of selected IGF1R/IR inhibitors alone or in combination with AR antagonists. Murine TNBC and QNBC implants will be established in nude as well as immune-competent mouse models and later, if effective, patient-derived TNBC xenograft (PDX) models in NSG-SGM3 mice will be used to assess combination therapies with immune checkpoint inhibitors combined with IGF1R inhibitors alone or with IGF1R/AR antagonist combinations.

General Design

There are significant antitumor effects in vivo using BMS-754807 (FIG. 6.) or in combination with NVP-AEW541 (FIG. 5B) using TNBC xenograft murine models. The in vivo effects of IGF1R/IR inhibitors alone and in combination with enzalutamide will be assessed and their coordinated effects with checkpoint inhibitors and the duration of their inhibitory effects post-treatment.

TNBC Models In Vivo. Nude Mice

TNBC cells will be implanted in mammary fat pads of nude mice. After tumors achieve an average size of 100-150 cm3, mice (8-10/group) will be randomized to groups: (a) vehicle (control), (b) BMS-754807, c) NVP-AEW541, and d) BMS-754807+NVP-AEW541 with each given by oral gavage daily. Enzalutamide alone and in combination with IGF1R antagonists will be included for testing. Since cell viability and proliferation assays suggest significant antitumor efficacy of BMS-754807, a dual IGF1R/IR antagonist, it will be assessed first in planned in vivo studies. Tumors will be measured every 2-3 days, with therapy given until tumors reach limiting sizes or to day 28. At the end of the first 28 days, some mice will be anesthetized using isoflurane, with blood collected by approved methods, while others will be maintained for another 14 days without combination therapy to assess continued tumor regression or growth. At the end of the additional 14-day period, animals will then be euthanized by established guidelines, with samples collected for comparison to controls. Final tumor weights and sizes of xenografts will be compared among groups. For biomarker analyses, formalin-fixed TNBC tissue will be paraffin-embedded, sectioned and placed on slides. IHC assay of AMPK, S6, IGF1R/IR phosphorylation, pAKT, AR and Ki-67 is planned. Blood plasma levels of IGF1, IGF2 and insulin will be tested using Rat/Mouse IGF ELISAs and Rat/Mouse Insulin ELISA (Millipore), using plasma from mice at the end of xenograft studies. Standard assays will be done to assess blood factors including CBC/electrolytes/Cr, glucose, lactate, and liver function54.

Murine TNBC Model in Syngeneic BALB/c (Immune-Competent) Mice

Current TNBC clinical trials are underway evaluating the efficacy of anti-PD-L1 antibodies as immune checkpoint inhibitors for anti-TNBC therapy. Notably, murine 4T1 TNBC cells express PD-L132. 4T1 cells (2×105) will be implanted in mammary fat pads of 6-to-8 wk old female syngeneic BALB/c mice. After tumors grow to 100-150 mm3, mice (8/group) will be randomized to groups: (a) vehicle (control), (b) PD-L1 antibody, (c) BMS-754807, (d) BMS-754807+PD-L1 antibody, (e) NVP-AEW541 and (f) NVP-AEW541+PD-L1 antibody. Optimal analogue dosing for antitumor efficacy and lack of toxicity based on animal weight will be determined. Mice will be injected with anti-PD-L1 antibody (100 μg IP, e.g. days 0, 3, 7, 10)35. Tumors will be measured 2-3 times weekly, with treatment continued to 12-28 days or until tumors reach limiting sizes. At the end of studies, mice are euthanized, with tumors harvested and tumor weights/sizes compared among groups. Another set of treated mice will be maintained for 12-24 days and tumor growth will be assessed.

1) Analysis of Immune Cell Subpopulations in Murine Tumor Model

For both groups, analysis of immune cell subsets in tumors, spleens and lymphatics will be performed by mass cytometry (cyTOF, refer to Preliminary Data above). Briefly, tissues are collected by approved guidelines, with single-cell suspensions generated with a tumor dissociation kit using recommended enzymes as per standard protocols. Cells will be stained using a cocktail of antibodies such as CD11b+ Ly6G and Ly6C for MDSCs, CD25/FoxP3 for Tregs, and others, including prior staining to discriminate live/dead cells. Cells are washed and pellets reconstituted for acquisition using a third generation Helios™ system (Fluidigm), with data analysis using Cytofkit. Further, intracellular staining of active CD8+TILs that produce IL-2, TNFα, and IFNγ will be validated. Markers for different TILs populations will be evaluated (see results of initial studies in FIG. 6).

2) IHC Analyses for Murine Model:

Samples of freshly-isolated tumors will be snap-frozen in liquid N2, then processed by UCLA Pathology Labs for cryostat sectioning and anti-murine CD8 and PD-L1 IHC60. Additional markers to assess actions of drugs will include IHC tumor assays to assess apoptosis biomarkers, proliferation marker Ki-67, active caspase 3, pAMPK and MDSCs. Drug effects on expression of proteins key for immunosuppressive activity of MDSCs will be tested, such as CD39/CD73, arginase 1, iNOS, TGF-β, CHOP (stress sensor protein), IL-10 and others. These assays may identify key actions of the therapeutic combination in inhibiting TNBCs in vivo.

PDX Models

To understand effects of IGF1R/IR antagonists alone and with checkpoint inhibitors in TNBC models, TM00096 PDXs implanted in humanized NSG-SGM3 mice from Jackson Laboratories will be obtained. Mice (n=12) will be randomized to: a) BMS-754807, b) PD-L1 antibody, c) BMS-754807+PD-L1 antibody or d) control. Control mice will be of the same strain. Animals will be treated as above. Studies with combined therapies including enzalutamide or NVP-AEW541 will be planned for future work depending on results of Aim 2 experiments above.

Statistical Analysis

Tumor growth curves will be compared between groups using mixed-effects regression models. These models include terms for treatment (vehicle, IGF1R/IR inhibitor, enzalutamide and combination groups, time and treatment by time interaction effects. One-way ANOVA, followed by Tukey post-hoc tests will be performed to compare final tumor weights/sizes and biomarkers across each group. The Kruskal-Wallis test is used to compare ordinal or skewed outcome measures between groups. To correct for multiple comparisons in evaluating marker outcomes, q-values are used to control the false discovery rate. The sample size (8 mice/group) will have 80% power to detect an effect size of at least 1.51 using a two group Student's t-test with a 0.05 two-sided significance level. The t-test is a simplification of the linear mixed effects model analysis plan. Our pilot data find effect sizes >1.5 suggesting that this study will be sufficiently powered.

Impact/Integration

Preliminary data indicate that selected IGF1R/IR inhibitors can effectively stop human TNBC progression in preclinical models in vivo. Indeed, TNBCs may well be uniquely sensitive to this class of antitumor therapeutics. Further, BMS-754807, a dual IGF1R/IR antagonist, may be re-purposed not only as a targeted antitumor agent for management of TNBC but also as an indirect agent to promote the antitumor activity of immune checkpoint inhibitors. These findings suggest that BMS-754807 can modulate the activity of specific immune cell subpopulations (such as effector and TCM TILs and MDSCs).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of treating breast cancer in a subject in need thereof, comprising conjointly administering an inhibitor of insulin receptor (IR) and an immune checkpoint inhibitor to the subject, wherein the breast cancer is triple negative breast cancer.

2. The method of claim 1, wherein the method further comprises conjointly administering an inhibitor of insulin-like growth factor 1 receptor (IGF1R) to the subject.

3. The method of claim 2, wherein the inhibitor of IGF1R is selected from dalotuzumab, MK-2206, ridaforolimus, MK-0752, NVP-AEW541, cetuximab, irinotecan, cisplatin, etoposide, figitumumab, carboplatin, paclitaxel, dexamethasone, docetaxel, prednisone, everolimus, ganitumab, exemestane, fulvestrant, folfiri, gemcitabine, panitumumab, sorafenib, linsitinib, R1507, and BMS-754807 or a pharmaceutically acceptable salt thereof; or a combination of any of the foregoing.

4. The method of claim 2, wherein the inhibitor of IGF1R is BMS-754807.

5. The method of claim 1, wherein the inhibitor of IR is selected from linsitinib, ceritinib, BMS-754807, S961 TFA, S961, BMS-536924, NVP-AEW541, AGL-2263, GSK1838705A, NVP-TAE 226, AG1024, MSDC 0160, NVP-ADW742, kaempferitrin, rhoifolin, and KU14R or a pharmaceutically acceptable salt thereof.

6. The method of claim 1, wherein the inhibitor of IR is BMS-754807.

7. The method of claim 1, wherein the immune checkpoint inhibitor is an inhibitor of CD27, CD28, CD80, CD86, CD40, CD122, CD137, OX40, GITR, ICOS, A2AR, B7-HR, BTLA, CTLA-4, IDO, KIR, LAG3, NOX2, PD-1, PD-L1, PD-L2, TIM-3, VISTA, or SIGLEC7.

8. The method of claim 1, wherein the immune checkpoint inhibitor is an inhibitor of PD-L1.

9. The method of claim 1, wherein the immune checkpoint inhibitor is an antibody or a small molecule.

10. The method of claim 9, wherein the immune checkpoint inhibitor is a polyclonal antibody, an intact monoclonal antibody, an antibody fragment, a single chain Fv (scFv), a chimeric antibody, a humanized antibody, or a fusion protein.

11. The method of claim 1, wherein the immune checkpoint inhibitor is selected from anti-CD274/B7-H1/PD-L1 clone 10F.9G2, atezolizumab, avelumab, cemiplimab, durvalumab, nivolumab, pembrolizumab, KB035, CK-301, AUNP12, CA-170, and BMS-986189 or a pharmaceutically acceptable salt thereof.

12. The method of claim 1, wherein the method further comprises conjointly administering an androgen receptor (AR) antagonist to the subject.

13. The method of claim 12, wherein the AR antagonist is selected from 17α-hydroxyprogesterone, chlormadinone acetate, cyproterone acetate, megestrol acetate, osaterone acetrate, 19-norprogesterone, nomegestrol acetate, 10-nortestosterone, dienogest, oxendolone, 17α-spirolactone, drospirenone, spironolactone, medrogestone, bicalutamide, flutamide, nilutamide, apalutamide, darolutamide, enzalutamide, proxalutamide, cimetidine, and topilutamide or a pharmaceutically acceptable salt thereof.

14. The method of claim 12, wherein the AR antagonist is enzalutamide or a pharmaceutically acceptable salt thereof.

15. The method of claim 1, wherein the breast cancer is quadruple negative breast cancer.

16. The method of claim 1, wherein the triple negative breast cancer is relapsed or refractory.

17. The method of claim 1, wherein the subject is a woman.

18. The method of claim 1, wherein the triple negative breast cancer is metastatic.

19. The method of claim 1, wherein the subject has a familial history of breast cancer.

* * * * *